(12) United States Patent
Ariza

(10) Patent No.: US 8,876,799 B1
(45) Date of Patent: *Nov. 4, 2014

(54) VASER ASSISTED HIGH DEFINITION LIPOSCULPTURE

(76) Inventor: Alfredo Ernesto Hoyos Ariza, Miami, FL (US)

( * ) Notice: Subject to any disclaimer, the term of this patent is extended or adjusted under 35 U.S.C. 154(b) by 289 days.

This patent is subject to a terminal disclaimer.

(21) Appl. No.: 13/461,027

(22) Filed: May 1, 2012

Related U.S. Application Data

(63) Continuation-in-part of application No. 12/287,816, filed on Oct. 14, 2008, now Pat. No. 8,167,868.

(51) Int. Cl.
*A61M 1/00* (2006.01)

(52) U.S. Cl.
USPC ........................................................ 604/542

(58) Field of Classification Search
CPC ................ A61B 2017/00792; A61M 2202/08
USPC ........................................................ 604/542
See application file for complete search history.

(56) References Cited

U.S. PATENT DOCUMENTS

| | | |
|---|---|---|
| 2,492,489 A | 7/1948 | Levinthal |
| 4,679,261 A | 7/1987 | Stanley et al. |
| 5,102,127 A | 4/1992 | Pohrer |
| 5,181,907 A | 1/1993 | Becker |
| 5,255,669 A | 10/1993 | Kubota et al. |
| 5,318,012 A | 6/1994 | Wilk |
| 5,329,943 A | 7/1994 | Johnson |
| 5,398,671 A | 3/1995 | Ortiz et al. |
| 5,419,761 A | 5/1995 | Narayanan et al. |
| 5,460,169 A | 10/1995 | Mouret |
| 5,501,653 A | 3/1996 | Chin |
| 5,569,165 A | 10/1996 | Chin et al. |
| 5,643,198 A | 7/1997 | Cucin |
| 5,683,366 A | 11/1997 | Eggers et al. |
| 5,884,631 A | 3/1999 | Silberg |
| 5,935,143 A | 8/1999 | Hood |
| 6,071,260 A | 6/2000 | Halverson |
| 6,450,975 B1 | 9/2002 | Brennan et al. |
| 6,461,350 B1 | 10/2002 | Underwood et al. |
| 6,920,883 B2 | 7/2005 | Bessette et al. |
| 7,331,951 B2 | 2/2008 | Eshel et al. |
| 7,857,773 B2 | 12/2010 | Desilets et al. |
| 8,167,868 B1 | 5/2012 | Ariza |
| 2004/0186353 A1 | 9/2004 | Palermo |

(Continued)

OTHER PUBLICATIONS

Frank, Paul Jarrod. "Advances in faul-emulsifying technologis", European Dermatology, vol. 3, 2008.*

(Continued)

*Primary Examiner* — Susan Su
(74) *Attorney, Agent, or Firm* — Malloy & Malloy, P.L.

(57) ABSTRACT

A surgical procedure for performing liposculpture on the human body comprising defining a surgical site where the liposculpture is to be performed including substantially 360 degrees about at least the torso portion of the body and/or the limbs. The surgical site is infiltrated with a predetermined quantity of solution and multi-layer emulsification of fat deposits about the surgical site is subsequently performed utilizing technology comprising "vibration amplification of sound energy at resonance" or (VASER), wherein the multi-layer emulsification includes at least a superficial layer emulsification of fat deposits and a deep layer emulsification of fat deposits. Subsequently, a multi-layer liposuction extraction of the emulsified fat deposits is performed, wherein the multi-layer liposuction extraction comprises a deep layer liposuction; a superficial layer liposuction and an intermediate layer liposuction.

17 Claims, 1 Drawing Sheet

(56) References Cited

U.S. PATENT DOCUMENTS

| | | |
|---|---|---|
| 2004/0206714 A1 | 10/2004 | Jablow et al. |
| 2007/0060989 A1 | 3/2007 | Deem et al. |
| 2008/0195036 A1 | 8/2008 | Merchant et al. |
| 2009/0248004 A1 | 10/2009 | Altshuler et al. |
| 2010/0155349 A1 | 6/2010 | Murphy |
| 2013/0066155 A1 | 3/2013 | Keating et al. |

OTHER PUBLICATIONS

Hoyos et al., VASER-Assisted High-Definition Liposculpture, Aesthetic Surgery Journal, 2007, 27:594-604 (Nov./Dec. 2007).

Gasperoni et al., Rationale of Subdermal Superficial Liposuction Related to the Anatomy of Subcutaneous Fat and the Superficial Fascial System 19:13-20 (1995).

Avelar, Regional Distribution and Behavior of the Subcutaneous Tissue Concerning Selection and Indication for Liposuction, 13:155-165 (1989).

Fischer, Chapter 22: Liposuction of the Trunk, Liposuction Principles and Practice, Springer-Verlag Berling Heidelberg, 2006.

Pitanguy et al., Chapter 23: Liposuction and Dermolipectomy, Liposuction Principles and Practice, Springer-Verlag Berling Heidelberg, 2006.

de la Torr et al., Chapter 24: The Modern Lipoabdominosplasty, Liposuction Principles and Practice, Springer-Verlag Berling Heidelberg, 2006.

Raskin, Chapter 25: Abdominal Liposuction in Colostomy Patients, Liposuction Principles and Practice, Springer-Verlag Berling Heidelberg, 2006.

Raskin, Chapter 27: Microcannula Liposuction, Liposuction Principles and Practice, Springer-Verlag Berling Heidelberg, 2006.

Gasparotti, Chapter 29, Three-Dimensional Superficial Liposculpture for Aged and Relaxed Skin, Liposuction Principles and Practice, Springer-Verlag Berling Heidelberg, 2006.

Cimino, Chapter 34: VASER—Assisted Lipoplasty: Technology and Technique, Liposuction Principles and Practice, Springer-Verlag Berling Heidelberg, 2006.

Giuseppe, Alberto, Chapter 35: Ultrasound-assisted lipoplasty for face contouring with VASER, Liposuction Principles and Practice, Springer-Verlag Berling Heidelberg, 2006.

Cimino, William, Chapter 32: Ultrasound-assited lipsuction: past, present, and future, Liposuction Principles ad Practice, Springer-Verlag Berling Heidelberg, 2006.

* cited by examiner

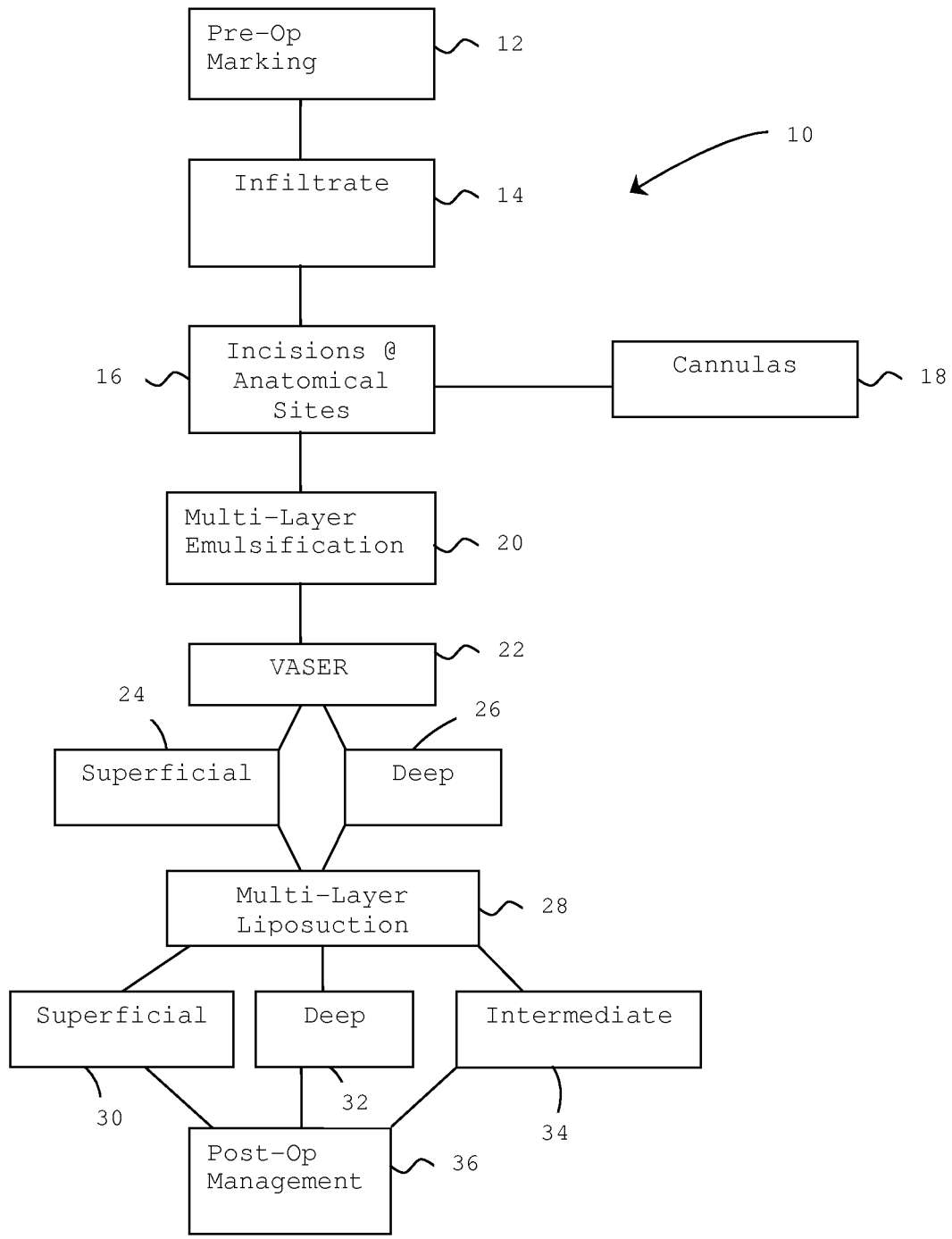

VASER ASSISTED HIGH DEFINITION LIPOSCULPTURE

CLAIM OF PRIORITY

The present application is a continuation-in-part application of previously filed, now pending application having Ser. No. 12/287,816, filed on Oct. 14, 2008 incorporated herein by reference, which has issued into U.S. Pat. No. 8,167,868 on May 1, 2012.

BACKGROUND OF THE INVENTION

1. Field of the Invention

The present invention is directed to a surgical procedure for accomplishing liposculpturing of the human body which incorporates the use of "VASER" technology or "vibration amplification of sound energy of resonance". Inclusive in the surgical procedure is the multi-layer emulsification of fat deposits about a surgical site associated with a portion of the body, including at least the torso of the body and/or one or more selected limbs of the body, wherein the surgical site may extend substantially 360° about the selected body portion. Multi-layer liposuction is utilized to extract the emulsified fat deposits resulting in a three-dimensional technique which enhances the natural muscularity of the patient's body.

2. Description of the Related Art

Lipoplasty is currently the plastic surgical procedure performed most often in the United States, wherein the fundamental technique and technology associated therewith have changed only slightly during the past 30 years. Superficial lipoplasty with standard lipoplasty cannulas expand the boundaries of body contouring by enabling the removal of fat from superficial layers. However, this advance in lipoplasty technique has also involved increased risk of scarring and contour irregularities.

Existing publications indicate that traditional lipoplasty techniques often fail to achieve the aesthetic goal of a "wash board" abdominal contour because sub-dermal fat often obscures the muscular detail. Known techniques referred to as "abdominal etching" use different lipoplasty to detail abdominal musculature, specifically the rectus abdominis muscle, between the linea alba and the linea semilunaris, while also addressing the tendinous inscriptions of the rectus abdominis muscle. However, abdominal etching was designed specifically for the male body having between 8% and 15% body fat and was limited to only interior abdominal wall. Accordingly, female and/or moderately obese patients were not susceptible subjects for the known abdominal etching surgical procedure.

Therefore, there is a need in the area of body sculpturing for a high definition liposculpture surgical procedure which would represent a significant improvement in body contouring. As such, the terms "liposculpture" is utilized to define a surgical technique which does not simply remove fat, but represents an "artistic approach" designed to emulate surface anatomy. Accordingly, a proposed improvement in this area would include "high definition liposculpture" (HDL), which represents a development through the study of art and anatomy of the human musculature as an artistic treatment of the human form to create not only a slim figure but also the appearance of a highly developed musculature. Further, a proposed HDL procedure elevates the concept of abdominal etching to a three-dimensional approach taking into account the contributions made by other muscle groups to integrate the entire or substantially 360 degrees of the torso and in certain instances the limbs, including the legs or arms, as well as back of the body on which the surgical procedure is being performed. As a result, the differing aesthetic goals of male and female body contouring can be integrated into such a proposed procedure which further includes key areas such as pectorals in men and the gluteal area in women.

Further, the proposed unique and improved surgical procedure for body sculpturing may appropriately incorporate the use of "VASER" technology or "Vibration Amplification of Sound Energy at Resonance" with the HDL procedure. This association represents a marriage between technology and technique that allows a more precise, less traumatic procedure with improved outcomes. Accordingly, VASER assisted HDL or "VAHDL" allows fat tissue to be prepared for more effective sculpturing through emulsification. As such, the surgeon can "sculpt" muscular anatomy in great detail through gentle extraction aspiration that minimizes the trauma normally associated with traditional lipoplasty. Further, VAHDL embodies the ultimate understanding of how superficial anatomy influences external appearance. As such, VAHDL has been developed through the study of "surface anatomy" of the human musculature much as an artist would view the human form and begins where superficial lipoplasty ends. In addition, the unique surgical procedure defined by VAHDL highlights the importance of contributions made to the aesthetics of the human form by both superficial and deep fat layers when these layers are properly proportioned both between and over the associated muscle groups.

SUMMARY OF THE INVENTION

The present invention is directed to a three-dimensional technique which enhances natural muscularity of the patient and includes transitioning, comprising an intermediate layer liposuction technique to facilitate the enhancement of intended results. As such, high definition liposculpture is utilized in combination with VASER technology to define the present invention comprising "VASER assisted high definition liposculpture" or "VAHDL".

The VAHDL procedure of the present invention preliminarily involves a preoperative surgical marking of a patient when in the operating room with the patient initially disposed in a supine position and completed with a patient in an upright standing position. As such, an understanding of superficial anatomy and human typography is important, thereby requiring the surgeon to learn how to examine the patient for individual characteristics in order to avoid inaccurate marking which could possibly lead to deformities and abnormal appearance. In the application of the VAHDL procedure, it is to be noted that the surface anatomy varies between men and women. In women, the transversal lines in the rectus abdominis muscle are not aesthetically desirable because they tend to look too "masculine". In men, the landmarks marked may preferably include pectorals major, serratus interior, rectus abdominis, external oblique, iliac crest and inguinal ligaments as well as the relationship between these structures.

Further, the VAHDL surgical procedure of the present invention comprises both a superficial and deep infiltration performed using solution of 1,000 cc of normal saline as well as 1 cc of epinephrine. Detailed infiltration may be performed in areas that require more superficial works, such as the waist and perigluteal area in women and other areas in the male body. Further, in anticipation of the use of VASER technology, the exact amounts of infiltration in each area and the estimated time of VASER use are determined and maintained.

The VASER technology is a primary technique for accomplishing emulsification of predetermined fat deposits. Further, the emulsification technique using VASER technology is performed preferably in a continuous mode for the high de-bulking and in a pulsed mode at lower power for more delicate areas and the immediate sub-dermal plane. Preferably, the de-bulking was performed using ventilated cannulas, beginning in the deep layers and continuing to the mid-lamellar layer and between muscle groups. Superficial emulsification was performed to define the relevant anatomy of the muscle groups in each treatment area. Transitioning was then performed to define the superficial anatomy landmarks. As used herein "transitioning" comprises the de-bulking or extracting of some of the remaining fat deposits existing over the associated muscle groupings and smoothing the surfaces over the associated anatomical areas, such as the mid-lamellar area.

Accordingly, the VAHDL surgical procedure of the present invention comprises a multi-layer emulsification technique comprising both deep layer emulsification of fat deposits and superficial layer emulsification of fat deposits using VASER technology, as described in greater detail herein. Subsequently, multi-layer liposuction is applied to accomplish a more specific definition of the relative anatomy of the muscle groups in each anatomical section of the surgical site, as well as the transitioning of anatomy landmarks by removing the remaining fat over predetermined muscle groups specifically, but not exclusively, in the mid-lamellar area.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a schematic representation in block diagram form representing related and cooperative surgical steps and techniques which collectively define the "VASER assisted high definition liposculpture" or "VAHDL" surgical procedure of the present invention.

Like reference numerals refer to like parts throughout the several views of the drawings.

DETAILED DESCRIPTION OF THE PREFERRED EMBODIMENT

The present invention is directed to a VASER assisted high definition liposculpture surgical procedure and is a three-dimensional technique which enhances the natural muscularity of the patient resulting in the creation not only of a slim figure for the human body but also the appearance of highly developed muscularity. As such, the VASER assisted high definition liposculpture or "VAHDL" is applicable for use on both men and women with less limitations relating to body physique, age, gender, etc. than known or conventional body sculpturing techniques. Distinguishing features of the VAHDL procedure include the use of underlying anatomical structures as a guide to accomplishing the intended three-dimensional body contour.

Further, while the surgical site, in at least one embodiment of the present invention represents 360 degrees about at least the torso portion of the human body, this three-dimensional approach can also take into account the contributions made by other muscle groups to integrate and further define the surgical site to include substantially the entire torso, back and limbs including the legs and arms. The subject VAHDL surgical procedure in the various preferred embodiments of the present invention utilizes the assistance of "vibration amplification of sound energy at resonance" or "VASER" technology. In utilizing VASER technology, the VAHDL surgical procedure enables the application of lipoplasty techniques to the superficial fat layers or deposits and overcomes certain disadvantages associated with "abdominal etching" which has limited applicability in terms of gender and obesity of qualified patients.

More specifically, VASER technology as applied to the subject VAHDL surgical procedure is preferably performed utilizing a solid probe that generates ultrasound on various multi-layers for purposes of emulsifying fat deposits. As set forth in greater detail, VASER technology is used in the performance of multi-layer emulsification of fat deposits at and substantially about 360° of the surgical site. Subsequently multi-layer liposuction was applied to the various anatomical sections to extract the emulsified fat deposits thereby accomplishing the desired sculpturing and muscularity of the patient about the 360° surgical site.

With primary reference to the schematic representation of the accompanying FIGURE, the VAHDL surgical procedure is generally indicated as 10 and initially comprises preoperative marking 12 of the patient. At least partially dependent on the selected surgical site, the preoperative marking 12 is preferably performed with the patient initially supine and completed with the patient in an upright standing position. Subsequent to the preoperative marking 12, an infiltration of the body about the surgical site, which may include substantially 360° about the surgical site, is accomplished, as at 14. More specifically, the infiltration technique or process 14 comprises the infiltration of a predetermined quantity of saline solution, such as substantially 1,000 cc, and epinephrine, in a predetermined quantity, such as generally 1 cc. This solution is infiltrated about the surgical site, which may include substantially 360° about the surgical site, by performing a plurality of anatomical incisions 16 through which the fluid is introduced using infiltration cannulas 18.

Subsequent to the infiltration procedure, the additional, non-mobile step in the VAHDL surgical procedure involves emulsification, as at 20, and more specifically multi-layer emulsification at the surgical site, which may include substantially 360° about the surgical site. As set forth above, the emulsification of fat deposits is performed using VASER technology as at 22 and is preferably performed by a solid probe that generates ultrasound on superficial tissue layers and deep tissue layers. In a preferred embodiment emulsification may first be performed on superficial tissue layers and subsequently on the intermediate or deep tissue layers. The VASER probe generates a specific frequency that is selective to fat and accomplishes the emulsification of fat deposits in its path or as applied. Accordingly, with reference to the accompanying FIGURE, the emulsification 20, utilizing the VASER assisted technology 22 involves a multi-layer emulsification comprising at least a superficial layer emulsification of fat deposits, as at 24 and a deep layer emulsification of fat deposits, as at 26. By utilizing the VASER assisted technology 22, the multi-layer emulsification may also comprise a superficial layer emulsification of fat deposits, a deep layer emulsification of fat deposits, and an intermediate layer emulsification of fat deposits.

Thereafter, a multi-layer liposuction is performed for the extraction of the emulsified fat deposits, as at 28. The multi-layer liposuction is more specifically defined by accomplishing a superficial layer liposuction 30, a deep layer liposuction 32 and an intermediate layer liposuction 34. It should be noted that the order or sequence of applying the liposuction to the superficial, deep and/or intermediate layers may vary. A skilled surgeon therefore can accomplish liposuction at the different superficial, deep or intermediate layers in any preferred order or sequence and is not limited to the specific order of application.

Subsequently, postoperative management of the patient as at 36 is accomplished, as will be set forth in greater detail hereinafter.

In the development and perfection of the VAHDL surgical procedure of the present invention, a trial was performed utilizing 306 patients treated in two separate series. Satisfactory results were obtained in 257 patients or 84% of the patients involved in the trial. No cases of skin nacrosis occurred and minor complications included 20 cases of seroma or fluid build-up, nine cases of port site burns and five cases of prolonged swelling. The conclusions clearly indicated that the VAHDL or "VASER assisted high definition liposculpture" is an aggressive approach to body contouring that enables the surgeon to perform body sculpting of the superficial tissues to define the three-dimensional surface musculature in a wide range of patients.

Details of the surgical trial included a first step of preoperative marking performed when the patient is initially in a supine orientation and completed when the patient is an upright, standing position. During the preoperative marking, the physician should recognize that surface anatomy varies between men and women wherein the "V" shape is desirable in the male back as is a convexity over the inferior portion of the obliquus muscle. In women, the landmark may include the serratus interior, the rectus abdominis, the external oblique, the iliac crest and the inguinal ligaments.

In the infiltration procedure 14, as represented in the accompanying FIGURE, both superficial and deep infiltration were performed using a standard saline solution with the addition of epinephrine in indicated volumes as set forth above. Symmetric volumes were infiltrated about the surgical site and specifically on each side of the body torso. The infiltration aspiration ratio was 1.5-2:1. Detailed infiltration was performed in areas that required more superficial works such as the waist and perigluteal area in women, the indentation of the rectus and serratus muscles in men and the areas of skin laxity, such as the hypogastrium. In anticipation of the use of VASER technology, the exact amounts of infiltration in each area and the estimated time of VASER use were recorded. An estimated 10 minutes was allowed after infiltration before commencement of the VASER emulsification in order to allow time for effective vasoconstriction.

The emulsification procedure was performed in accordance with the chart of volume infiltrated in the same order as the infiltration. The duration of VASER treatment was 1 minute per each 100 mL of infiltration, but the clinical end point was the loss of resistance. Areas of high de-bulking, such as large fat deposits, were treated, utilizing VASER technology, with 3.7 mm or 2.9 mm, 3-groove probe, at 80% power in a continuous mode. The back and posterior arms were treated using a 3.7 mm, 1-groove probe in continuous mode. Thin skin or delicate areas such as the inner thighs, waist and neck were treated using a 2.9 mm, 3-groove probe at 60% power in a pulsed mode. Differential emulsification was performed for each muscle group and the muscle lines. Superficial emulsification was performed using a 2.9 mm, 3-groove probe, always in a pulsed mode. In some cases, additional infiltration was performed prior to the superficial emulsification. It was noted that the superficial emulsification addresses the immediate sub-dermal plane, thereby allowing enhanced skin retraction and compensating for areas of muscle or fascial laxity. The emulsification focused on three lamellar layers. The clinical end point in superficial layer emulsification was also the loss of resistance, but the skin was never allowed to become warmer than the hands of the surgeon. The achievement of loss of resistance in this layer without heat generation is a factor in avoiding complications.

In the associated de-bulking technique, ventilated cannulas with specialized small holes which prevent clogging achieved optimal efficiency and provided gentle suction that minimizes trauma. De-bulking began at the areas of fat deposits in the deep layer, using 3.7-mm or 4.6-mm cannulas and continued in the mid-lamellar layer and between muscle groups, avoiding aspiration against delicate sub-dermal layers.

Superficial emulsification and extraction steps were performed selectively over the muscular frame in each area to define relevant anatomy for each muscle group (i.e. linea alba and its tendinous insertions, the pectoral inferior line, inguinal ligament), using a 2.9-mm probe emulsification and 3.0-mm cannula aspiration. Superficial emulsification and extraction were performed in the sub dermal lamellar layer. From an artistic point of view this step is analogous to the initial two-dimensional sketch of any drawing.

The transitioning technique further comprises the blending of the framing and typography of the muscles. More specifically using a 3.7-mm or 4.6-mm cannula, some of the remaining fat deposits over each of the muscle grouping was de-bulked, while the surface overlying the creases over the mid-lamellar layer was smoothed, thus improving the definition of the superficial anatomy landmarks. Transitioning creates the natural but well defined appearance that was sought to be achieved. From an artistic point of view, the transitioning step is equivalent to the addition of "shadows and light" to create a three-dimensional "rendering". The surgical end point was the definition of the lateral borders of the muscles while retaining a thin layer of fat in the range of 1 cm in a pinch test.

In the postoperative management 36 open drains were left for 48-72 hours in the sacral area in female patients or in the inguinal area in male patients. Postoperative care included the use of a mild compression garment, deep vein thrombosis stockings and a cotton-lamented soft foam band, which may be used for a period of up to four weeks. Patients were given oral antibiotic and anti-inflammatory drugs for a short period of time. After 48 hours, patients were allowed to start postoperative lymphatic drainage massages and adjunctive external ultrasound of one hour sessions, once a day for ten days.

Patients were followed postoperatively at 1, 3, 6, 12 and 24 weeks. The anatomical definition accomplished at surgery was lost in the early initial postoperative period because of swelling. However, the accomplished definition started to reemerge at 3-4 weeks postoperative. Patients also experienced indurations during the first 6-8 weeks postoperatively that tended to be migratory, particularly in the areas of definition where contour was created by superficial and transitioning work. In all cases, these indurations disappeared completely by the third month. Patients also experienced cyclic swelling that varied the appearance of definition throughout the day. At approximately 4 months postoperatively, the swelling abated and patients could see about 95% of their final results and accomplished muscular definition.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A surgical procedure for performing liposculpture on the human body, said surgical procedure comprising:
    defining and marking a surgical site over a portion of at least one limb of the body,
    infiltrating a predetermined quantity of solution about the surgical site on the one limb,
    performing multi-layer emulsification of fat deposits about the surgical site on the at least one limb, including a superficial layer emulsification, an intermediate layer emulsification and a deep layer emulsification of fat deposits, and
    performing multi-layer liposuction extraction of emulsified fat deposits at the at least one limb, including a deep layer liposuction; a superficial layer liposuction and an intermediate layer liposuction.

2. A procedure as recited in claim 1 further defining and marking the surgical site as substantially 360° about the at least one limb of the body.

3. A procedure as recited in claim 1 comprising performing the multi-layer emulsification using VASER technology.

4. A procedure as recited in claim 1 wherein the infiltrated solution is epinephrine with a saline solution.

5. A procedure as recited in claim 1 further comprising forming a plurality of anatomical incisions over the surgical site and introducing the predetermined quantity of solution through the plurality of anatomical incisions.

6. A procedure as recited in claim 5 further comprising introducing the predetermined quantity of solution using infiltration cannulas.

7. A procedure as recited in claim 1 comprising accomplishing a sub-dermal superficial release of fat deposits and thereby produce skin retraction by performing the superficial layer emulsification of fat deposits.

8. A procedure as recited in claim 7 comprising creating predetermined anatomical landmarks by using underlying anatomical structures as a guide for a superficial layer emulsification.

9. A procedure as recited in claim 1 comprising extracting the fat deposits which primarily create deformities about the surgical site by performing the deep layer liposuction.

10. A procedure as recited in claim 9 comprising making the portion of the at least one limb correspond to predetermined anatomical landmarks of muscle tissue about the surgical site by performing the superficial layer liposuction.

11. A procedure as recited in claim 10 comprising distinguishing differences between surgically affected anatomical sections of the surgical site by performing the intermediate layer liposuction.

12. A procedure as recited in claim 1 further including transitioning superficial anatomy landmarks comprising extracting at least some remaining fat deposits existing over muscle groupings associated with the superficial anatomy landmarks and smoothing the surfaces over the associated superficial anatomy landmarks.

13. A surgical procedure for performing liposculpture on the human body, said surgical procedure comprising:
    defining and marking a surgical site along a portion of at least one limb of the body,
    infiltrating a predetermined quantity of solution about the surgical site on the at least one limb,
    performing multi-layer emulsification of fat deposits, using VASER technology, about the surgical site of the at least one limb including a superficial layer emulsification, an intermediate layer emulsification, and a deep layer emulsification of the fat deposits,
    performing multi-layer liposuction extraction of emulsified fat deposits at the surgical site, including a deep layer liposuction, a superficial layer liposuction and an intermediate layer liposuction, and
    transitioning superficial anatomy landmarks at the surgical site comprising extracting at least some remaining fat deposits existing over muscle groupings associated with the superficial anatomy landmarks and smoothing the surfaces over the associated superficial anatomy landmarks.

14. A procedure as recited in claim 13 further defining and marking the surgical site as substantially 360° about the at least one limb of the body.

15. A procedure as recited in claim 14 further comprising infiltrating the predetermined quantity of solution about the 360° surgical site on the at least one limb.

16. A procedure as recited in claim 15 further comprising performing the multi-layer emulsification of fat deposits about the 360° surgical site of the at least one limb.

17. A procedure as recited in claim 16 comprising defining the infiltrated solution as epinephrine combined with a saline solution.

* * * * *